(12) United States Patent
Matthiessen

(10) Patent No.: US 9,388,452 B2
(45) Date of Patent: Jul. 12, 2016

(54) METHODS FOR MODELING PROTEIN STABILITY

(75) Inventor: Peter Matthiessen, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 13/638,919

(22) PCT Filed: Apr. 8, 2011

(86) PCT No.: PCT/US2011/031821
§ 371 (c)(1),
(2), (4) Date: Feb. 26, 2013

(87) PCT Pub. No.: WO2011/127426
PCT Pub. Date: Oct. 13, 2011

(65) Prior Publication Data
US 2013/0171671 A1 Jul. 4, 2013

Related U.S. Application Data

(60) Provisional application No. 61/322,204, filed on Apr. 8, 2010.

(51) Int. Cl.
| | | |
|---|---|---|
| *G01N 33/48* | (2006.01) | |
| *G01N 33/50* | (2006.01) | |
| *C12Q 1/56* | (2006.01) | |
| *G06F 19/16* | (2011.01) | |
| *G06F 17/10* | (2006.01) | |
| *G06F 17/11* | (2006.01) | |
| *G06F 19/12* | (2011.01) | |
| *C07K 14/755* | (2006.01) | |
| *C07K 14/81* | (2006.01) | |
| *G01N 33/68* | (2006.01) | |

(52) U.S. Cl.
CPC ............. *C12Q 1/56* (2013.01); *C07K 14/755* (2013.01); *C07K 14/8128* (2013.01); *G01N 33/6803* (2013.01); *G06F 17/10* (2013.01); *G06F 17/11* (2013.01); *G06F 19/12* (2013.01); *G06F 19/16* (2013.01); *G01N 2333/755* (2013.01); *G01N 2333/8128* (2013.01)

(58) Field of Classification Search
None
See application file for complete search history.

(56) References Cited

U.S. PATENT DOCUMENTS 5,583,209 A * 12/1996 Lollar et al. ............ 536/23.5
6,518,406 B1 * 2/2003 Winge .................... 530/393
2001/0012610 A1 * 8/2001 Bronshtein ............... 435/2
2004/0199138 A1 * 10/2004 McBay et al. ........... 604/403
2006/0105320 A1 * 5/2006 Lindquist et al. ....... 435/4
2007/0197439 A1 * 8/2007 Zhu et al. ................. 514/12
2007/0231315 A1 * 10/2007 Lichte et al. ............ 424/94.64

FOREIGN PATENT DOCUMENTS

DE 199 30 466 A1 1/2001

OTHER PUBLICATIONS

Breece et al. Solvent viscosity and protein dynamics. Biochemistry, vol. 19, 1980, pp. 5147-5157.*
Free energy, 2013, 2 pages. The Columbia Encyclopedia. Retrieved online on May 25, 2014 from <<http://www.credoreference.com>>.*
Bentley, D.L., "Statistical techniques in predicting thermal stability," *Journal of Pharmaceutical Sciences*, Apr. 1, 1970, vol. 59, No. 4, pp. 464-468.
Derek, J.H. et al., "Estimation of melting curves from enzymatic activity-temperature profiles," *Biotechnology and Bioengineering*, Nov. 20, 1993, vol. 42, No. 10, pp. 1245-1251.
Dyrstad, K. et al., "An opportunistic stability strategy; simulation with real data," *International Journal of Pharmaceutics*, Oct. 1, 1999, vol. 188, No. 1, pp. 97-104.
Ertel, K.D. et al., "Examination of modified Arrhenius relationship for pharmaceutical stability prediction," *International Journal of Pharmaceutics*, Jun. 11, 1990, vol. 61, No. 1-2, pp. 9-14.
Garrett, E.R., "Prediction of stability of drugs and pharmaceutical preparations," *Journal of Pharmaceutical Sciences*, Sep. 1, 1962, vol. 51, No. 9, pp. 811-833.
International Search Report mailed Sep. 28, 2011, for International Patent Application No. PCT/US2011/031821, 6 pages.
Maeda, N. et al., "The Unique Pentagonal Structure of an Archaeal Rubisco Is Essential for Its High Thermostability," *Journal of Biological Chemistry*, Aug. 23, 2002, vol. 277, No. 35, pp. 31656-31662.
Nelson et al., "Stability prediction using the Arrhenius model," *Computer Programs in Biomedicine*, Feb. 1, 1983, vol. 16, No. 1-2, pp. 55-60.
Nikolova, P.V. et al., "Thermostability and Irreversible Activity Loss of Exoglucanase/Xylanase Cex from Cellulomonas fimi +" *Biochemistry*, Feb. 1, 1997, vol. 36, No. 6, pp. 1381-1388.
Peterson, M.E., "A New Intrinsic Thermal Parameter for Enzymes Reveals True Temperature Optima," *Journal of Biological Chemistry*, Jan. 1, 2004, vol. 279, No. 20, pp. 20717-20722.

*Primary Examiner* — Russell S Negin
(74) *Attorney, Agent, or Firm* — Morgan Lewis & Bockius LLP

(57) ABSTRACT

The present invention relates to a method for determining the highest temperature that is suitable for performing accelerated protein stability studies, as well as to a method for modeling real-time protein stability from accelerated stability data generated at said temperature.

20 Claims, 4 Drawing Sheets

US 9,388,452 B2

METHODS FOR MODELING PROTEIN STABILITY

CROSS-REFERENCES TO RELATED APPLICATIONS

The present application claims the benefit of U.S. Provisional Application No. 61/322,204, filed Apr. 8, 2010, which is expressly incorporated herein by reference in its entirety for all purposes.

FIELD OF THE INVENTION

The present invention relates to a method for determining the highest temperature that is suitable for performing accelerated protein stability studies, as well as to a method for modeling real-time protein stability from accelerated stability data generated at said temperature.

BACKGROUND OF THE INVENTION

Stability studies are indispensable during the development of protein formulations. They are conducted inter alia to define the optimal storage conditions and expiration date of the final product.

To accelerate stability determinations, protein stability studies are often conducted at elevated temperatures. The key issue in interpreting the results of such accelerated protein stability studies is whether the data from accelerated studies can be extrapolated to those under real-time conditions.

Very often accelerated protein stability studies are performed at 40° C. Extrapolation of protein stability at temperatures different from that is based on an Arrhenius plot, wherein linearity of the Arrhenius plot is assumed. However, since protein stability Arrhenius plots in reality are often not linear at higher temperatures, this method can lead to wrong results.

Therefore, a need exists in the field to provide a method for determining the highest temperature that is suitable for performing accelerated protein stability studies. Further, a need exists in the field to improve current methods for modeling real-time protein stability from accelerated stability data, in order to achieve more accurate and reliable results.

SUMMARY OF THE INVENTION

It is an object of the present invention to provide a method for determining the highest temperature that is suitable for performing accelerated protein stability studies. It is also an object of the present invention to provide an improved method for modeling real-time protein stability from accelerated stability data generated at said temperature. In particular, the methods of the present invention can advantageously identify the linear part of a protein stability Arrhenius plot, and thus the highest temperature that should be appropriate for performing accelerated protein stability studies, by determining the short term stability of a specific protein in temperature stress tests.

Figure 1:
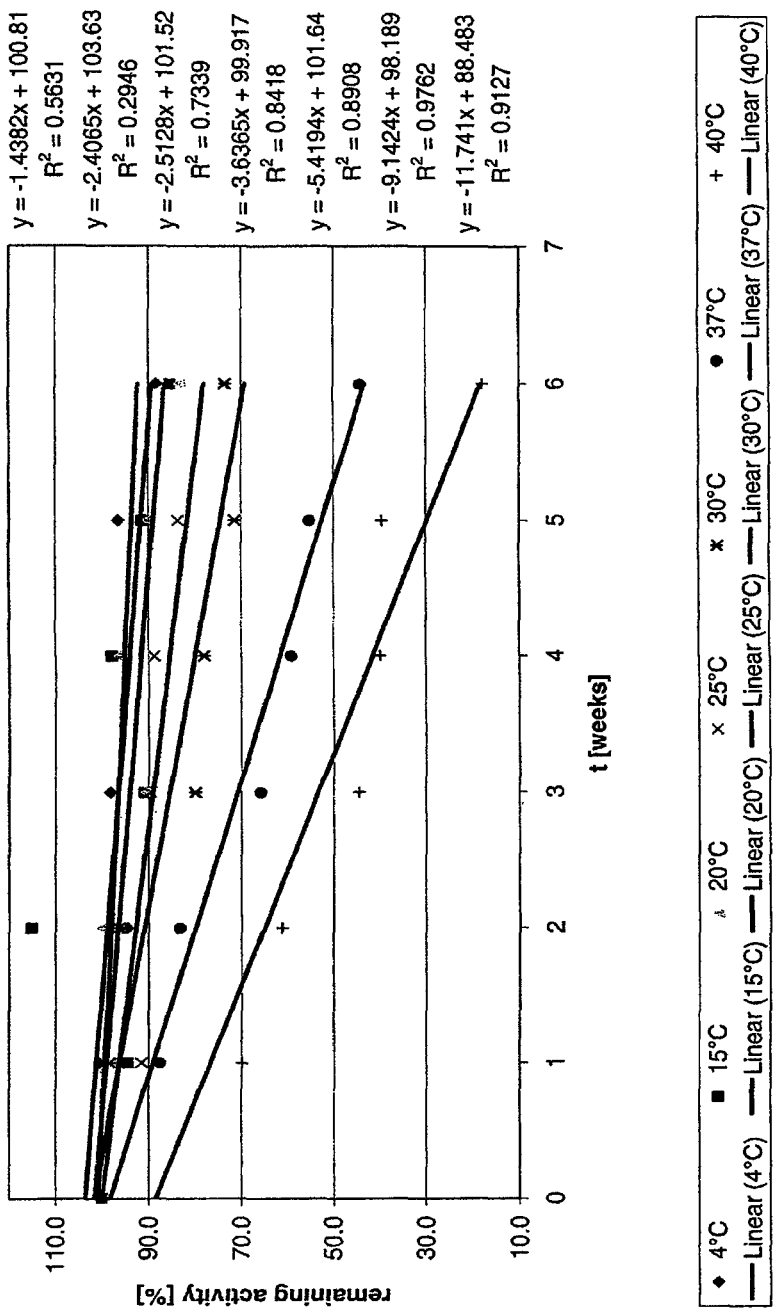
FIG. 1 shows the short term stability of a liquid Antithrombin III (AT III) formulation at different temperatures over time. The equations for the linear regression curves are shown. The rate constant of protein activity loss k corresponds to the negative ascent of these linear regression curves.

The present invention will be further illustrated in the following examples without being limited thereto.

DETAILED DESCRIPTION OF THE INVENTION

Background

Arrhenius plots and methods to establish these are known to a person skilled in the art. Briefly, the reciprocal temperature (1/T) is plotted against the natural logarithm of the rate constant (ln k) of protein stability loss at that temperature. Arrhenius plots for protein stability often exhibit a linear part and a non-linear part, the latter particularly at higher temperatures. Determining the linear part of an Arrhenius plot can be done visually in a straightforward manner. From the lowest 1/T value of the linear part of the Arrhenius plot, the corresponding highest temperature T can easily be calculated.

Methods for performing accelerated protein stability studies and determining real-time protein stability based on accelerated stability data are well known in the art.

Definitions

The term "protein" as used herein relates to any peptide, oligopeptide, polypeptide, monomeric protein, multimeric protein or multisubunit protein complex. For the purposes of the present invention, a protein may be isolated from a natural source (e.g., plasma-derived) or recombinantly produced. For example, in certain embodiments, the protein formulation comprises a plasma derived blood protein, such as an immunoglobulin, blood coagulation factor, or other protein found in primate plasma. Non-limiting examples of coagulation proteins, which may be purified from a natural source (i.e., plasma-derived) or expressed recombinantly, include, Factor II (prothrombin), Factor III (platelet tissue factor), Factor V, Factor VII, Factor VIII, Factor IX, Factor X, Factor XI, Factor XII, Factor XIII, von Willebrand Factor (vWF), Antithrombin III (AT III), Furin, and ADAMTS proteins (i.e., ADAMTS13). Non-limiting examples of other proteins found in the plasma of primates (i.e., humans), include complement factors (i.e., Factor H and Complement factors C1, C2, C2a, C2b, C3, C3a, C3b, C4, C4a, C4b, C5, C5a, and C5b), Alpha-1 antitrypsin (A1A), Albumin, and an Inter-alpha-trypsin Inhibitor (IαI). Other protein formulations of interest include antibodies and functional fragments thereof, including without limitation, antibodies or immunoglobulins purified from a natural source, recombinant antibodies, chimeric antibodies, huminized antibodies, and fragments thereof (i.e., an scFv, a Fab, a diabody, a triabody, a single-domain antibody, a recombinant antibody fragment, a tascFv; and a biscFv). In a preferred embodiment, the protein is a therapeutic protein.

As used herein, an "antibody" refers to a polypeptide substantially encoded by an immunoglobulin gene or immunoglobulin genes, or fragments thereof (i.e., an scFv, a Fab, a diabody, a triabody, a single-domain antibody, a recombinant antibody fragment, a tascFv; or a biscFv), which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

Non-limiting examples of antibody formulations include, plasma-derived immunoglobulin preparations, recombinant polyclonal or monoclonal preparations, minibodies, diabodies, triabodies, antibody fragments such as Fv, Fab and F(ab)2 or fragmented antibodies such as monovalent or multivalent single chain Fvs (scFv, sc(Fv)$_2$, minibodies, diabodies, and triabodies such as scFv dimers) in which the variable regions of an antibody are joined together via a linker such as a peptide linker, and the like. Recombinant antibodies include murine antibodies, rodent antibodies, human antibodies, chimeric human antibodies (e.g., human/murine chimeras), humanized antibodies (e.g., humanized murine antibodies), and the like. In preferred embodiments, the recombinant antibody is a human, chimeric human, or humanized antibody suitable for administration to a human.

An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "protein stability" as used herein is used in a structural context, i.e. relating to the structural integrity of a protein, or in a functional context, i.e. relating to a protein's ability to retain its function and/or activity over time.

As used herein, "activity" refers to a functional activity or activities of a polypeptide or portion thereof associated with a full-length (complete) protein. Functional activities include, but are not limited to, biological activity, catalytic or enzymatic activity, antigenicity (ability to bind or compete with a polypeptide for binding to an anti-polypeptide antibody), immunogenicity, ability to form multimers, and the ability to specifically bind to a receptor or ligand for the polypeptide.

As used herein, the term "time of stability" refers to the length of time a formulation is considered stable. For example, the time of stability for a composition may refer to the length of time for which the level of protein aggregation and/or degradation in the composition remains below a certain threshold (e.g., 1%, 2%, 3%, 4%, 5%, 6%, 7%, 8%, 9%, 10%, 11, 12, 13, 14, 15, 16, 17, 18, 19, 20, etc.), the length of time a composition maintains an enzymatic activity above a certain threshold (e.g., 100%, 95%, 90, 85, 80, 75, 70, 65, 60, 55, 50, etc. of the amount of activity present in the composition at the start of the storage period), or the length of time a composition maintains an antigenic titer (e.g., 100%, 95%, 90, 85, 80, 75, 70, 65, 60, 55, 50, etc. of the antigenic titer present in the composition at the start of the storage period).

As used herein, the term "about" denotes an approximate range of plus or minus 10% from a specified value. For instance, the language "about 20%" encompasses a range of 18-22%.

As used herein, "storage" means that a formulation is not immediately administered to a subject once prepared, but is kept for a period of time under particular conditions (e.g. particular temperature, etc.) prior to use. For example, a liquid formulation can be kept for days, weeks, months or years, prior to administration to a subject under varied temperatures such as refrigerated (0° to 10° C.) or room temperature (e.g., temperature up to about 32° C.).

As used herein, "shelf-life" refers to the period of time a protein solution maintains a predetermined level of stability at a predetermined temperature in the formulation. In particular embodiments, the predetermined temperature refers to refrigerated (0° to 10° C.) or room temperature (e.g., temperature up to about 32° C.) storage.

Embodiments

Due to time considerations, protein stability assays are routinely performed at higher temperatures than those at which a therapeutic protein formulation will ultimately be stored at prior to administration. It has been found herein that protein stability calculations derived from accelerated protein stability assays performed at high temperatures are unreliable due to the non-linear relationship between temperature and protein stability. As such, a balance must be struck between minimizing the time it takes to determine the stability of a particular protein formulation and obtaining accurate extrapolations for the stability of the formulation at a given temperature.

Advantageously, the present invention provides, among other aspects, methods that allow for rapid and accurate determination of the stability of a protein formulation at a desired temperature. In certain embodiments, the present invention provides methods for accurately determining the stability of a protein formulation. In a specific embodiment, the methods provided herein are suitable for evaluation pharmaceutical protein formulations. For examples, the methods provided herein may be used to determine which formulation(s), of a plurality of formulations, are best suited for storage at a desired temperature.

Methods for Determining Temperatures Suitable for Protein Stability Studies

In one aspect, the present invention relates to a method for determining the highest temperature that is suitable for performing accelerated protein stability studies, comprising the steps:
(a) establishing an Arrhenius plot of protein stability;
(b) identifying the linear part of the Arrhenius plot established in step (a); and
(c) determining the highest temperature underlying the linear part of the Arrhenius plot determined in step (b).

In a preferred embodiment, establishing the Arrhenius plot in step (a) comprises the sub-steps of: (a1) determining short term protein stability within a specific temperature range; and (a2) plotting the data obtained in step (a1) in an Arrhenius plot.

In another preferred embodiment, determining short term protein stability comprises determining protein stability over the course of 1 to 12 weeks. In another embodiment, determining short term protein stability comprises determining protein stability over the course of 2 to 8 weeks. In yet another embodiment, determining short term protein stability comprises determining protein stability over the course of 6 weeks.

In yet other, non-limiting embodiments, determining short term protein stability comprises determining protein stability over the course of weeks, i.e., 1, 2, 3, 4, 5, 6, 7, 8, 9, 10, 11, or 12 weeks; or months, i.e., 1, 2, 3, 4, 5, 6, 7, 8, 9, 10, 11, 12, 13, 14, 15, 16, 17, 18, 19, 20, 21, 22, 23, 24, 27, 30, 33, 36, or more months.

In yet another preferred embodiment, short term protein stability is determined in the temperature range of 4° C. to 60° C. In another embodiment, the temperature range is between 20° C. and 60° C. In another embodiment, the temperature range is between 20° C. and 40° C. In another embodiment, the temperature range is between 4° C. and 40° C.

In yet another embodiment, the temperature range is between 10° C. and 40° C. In another embodiment, the temperature range is between 15° C. and 40° C. In another embodiment, the temperature range is between 20° C. and 40° C. In another embodiment, the temerature range is between 4° C. and 35° C. In yet another embodiment, the temperature range is between 10° C. and 35° C. In another embodiment, the temperature range is between 15° C. and 35° C. In another embodiment, the temperature range is between 20° C. and 35° C. In another embodiment, the temerature range is between 4° C. and 30° C. In yet another embodiment, the temperature range is between 10° C. and 30° C. In another embodiment, the temperature range is between 15° C. and 30° C. In another embodiment, the temperature range is between 20° C. and 30° C. The temperature range employed will depend upon various factors, including but not limited to, the desired storage temperature, the general stability of the protein(s) present in the formulation, the desired mode of administration, and the like.

In yet another preferred embodiment of the methods of the present invention, short term protein stability is determined at 5° C. intervals. In other embodiments, the short term protein stability is determined at 1° C. intervals, or 2° C., 3° C., 4° C., 5° C., 6° C., 7° C., 8° C., 9° C., 10° C., 11° C., 12° C., 13° C., 14° C., 15° C., or greater intervals.

In one embodiment, protein stability is measured by determining the level of enzymatic activity (e.g., the loss in activity) over a given time period. In another embodiment, protein stability is measured by determining the level of protein or substrate binding over a given period of time. In another embodiment, protein stability is measured by determining the level of protein oligomerization over a given time period. In yet another embodiment, particularly where the protein is an antibody, protein stability is measured by determining the anti-antigen titer over a given period of time. In another embodiment, protein stability is measured by determining the level of protein degradation over a given time period. In other embodiments, protein stability is measured by determining two, three, or four of the above stability metrics. Suitable binding and enzymatic activity assays will vary depending upon the protein present in the formulation. Many standard assays are well known in the art and the skilled artisan will readily be able to determine a suitable assay to measure the stability of a given protein formulation.

In one embodiment, the protein is an antibody or functional fragment thereof. In one embodiment, the antibody is selected from the group consisting of plasma-derived immunoglobulin preparations, recombinant polyclonal or monoclonal preparations, minibodies, diabodies, triabodies, antibody fragments such as Fv, Fab and F(ab)2 or fragmented antibodies such as monovalent or multivalent single chain Fvs (scFv, sc(Fv)2, minibodies, diabodies, and triabodies. In a specific embodiment, the antibody is a recombinant antibody. In another specific embodiment, the antibody is a chimeric antibody. In yet another specific embodiment, the antibody is a humanized antibody. In a preferred embodiment, the antibody is a therapeutic antibody. In another preferred embodiment, the antibody is a diagnostic antibody.

In another embodiment, the protein is a plasma-derived protein. In one embodiment, the plasma-derived protein is selected from the group consisting of Factor II (prothrombin), Factor III (platelet tissue factor), Factor V, Factor VII, Factor VIII, Factor IX, Factor X, Factor XI, Factor XII, Factor XIII, von Willebrand Factor (vWF), Antithrombin III (AT III), Furin, an ADAMTS proteins (i.e., ADAMTS13), a complement factor (i.e., Factor H and Complement factors C1, C2, C2a, C2b, C3, C3a, C3b, C4, C4a, C4b, C5, C5a, and C5b), Alpha-1 antitrypsin (A1A), Albumin, and an Inter-alpha-trypsin Inhibitor (IαI). In one embodiment, the plasma-derived protein is a coagulation factor. In a specific embodiment, the coagulation factor is Factor VIII. In another specific embodiment, the coagulation factor is AT III.

In another embodiment, the protein is a recombinant protein. In one embodiment, the protein is a recombinant blood protein. In one embodiment, the recombinant blood protein is selected from the group consisting of Factor II (prothrombin), Factor III (platelet tissue factor), Factor V, Factor VII, Factor VIII, Factor IX, Factor X, Factor XI, Factor XII, Factor XIII, von Willebrand Factor (vWF), Antithrombin III (AT III), Furin, an ADAMTS proteins (i.e., ADAMTS13), a complement factor (i.e., Factor H and Complement factors C1, C2, C2a, C2b, C3, C3a, C3b, C4, C4a, C4b, C5, C5a, and C5b), Alpha-1 antitrypsin (A1A), Albumin, and an Inter-alpha-trypsin Inhibitor (IαI). In one embodiment, the recombinant blood protein is a coagulation factor. In a specific embodiment, the coagulation factor is Factor VIII. In another specific embodiment, the coagulation factor is AT III.

In one embodiment, wherein the protein is recombinant, the protein is further modified. In a specific embodiment, the protein is modified by conjugation to a water soluble polymer. In one embodiment, the water soluble polymer is selected from a polyalkylene glycol (PAG), a polyethylene glycol (PEG), a hydroxyalkyl starch (HAS), a hydroxyethyl starch (HES), polysialic acid (PSA), and a sugar (e.g., glycosylation).

Accordingly, in another aspect the present invention relates to a method for determining the highest temperature that is suitable for performing accelerated protein stability studies, comprising the steps:
(a) determining short term protein stability over the course of 1 to 12 weeks within a temperature range of 4° C. to 60° C. at 5° C. intervals;
(b) plotting the data obtained in step (a) in an Arrhenius plot;
(c) identifying the linear part of the Arrhenius plot obtained in step (b); and
(d) determining the highest temperature underlying the linear part of the Arrhenius plot determined in step (c).

In a preferred embodiment, establishing the Arrhenius plot in step (a) comprises the sub-steps of: determining short term protein stability within a specific temperature range; and plotting the data obtained in step (a1) in an Arrhenius plot.

Methods for Modeling Real-Time Protein Stability

In another aspect, the present invention relates to a method for modeling real-time protein stability, comprising the steps:
(a) establishing an Arrhenius plot of protein stability;
(b) identifying the linear part of the Arrhenius plot established in step (a);
(c) determining the highest temperature underlying the linear part of the Arrhenius plot determined in step (b);
(d) performing accelerated stability studies at the temperature determined in step (c); and
(e) determining real-time protein stability based on the accelerated stability data obtained in step (d).

In particular, the highest temperature underlying the linear part of the Arrhenius plot determined in step (b) of the above methods is the highest temperature that is suitable for performing accelerated protein stability studies.

In a preferred embodiment, establishing the Arrhenius plot in step (a) comprises the sub-steps of: (a1) determining short term protein stability within a specific temperature range; and (a2) plotting the data obtained in step (a1) in an Arrhenius plot.

In another preferred embodiment, determining short term protein stability comprises determining protein stability over the course of 1 to 12 weeks. In another embodiment, determining short term protein stability comprises determining protein stability over the course of 2 to 8 weeks. In yet another embodiment, determining short term protein stability comprises determining protein stability over the course of 6 weeks. In yet other, non-limiting embodiments, determining short term protein stability comprises determining protein stability over the course of weeks, i.e., 1, 2, 3, 4, 5, 6, 7, 8, 9, 10, 11, or 12 weeks; or months, i.e., 1, 2, 3, 4, 5, 6, 7, 8, 9, 10, 11, 12, 13, 14, 15, 16, 17, 18, 19, 20, 21, 22, 23, 24, 27, 30, 33, 36, or more months.

In yet another preferred embodiment, short term protein stability is determined in the temperature range of 4° C. to 60° C. In another embodiment, the temperature range is between 20° C. and 60° C. In another embodiment, the temperature range is between 20° C. and 40° C. In another embodiment, the temerature range is between 4° C. and 40° C. In yet another embodiment, the temperature range is between 10° C. and 40° C. In another embodiment, the temperature range is between 15° C. and 40° C. In another embodiment, the temperature range is between 20° C. and 40° C. In another embodiment, the temerature range is between 4° C. and 35° C. In yet another embodiment, the temperature range is between 10° C. and 35° C. In another embodiment, the temperature range is between 15° C. and 35° C. In another embodiment, the temperature range is between 20° C. and 35° C. In another embodiment, the temerature range is between 4° C. and 30° C. In yet another embodiment, the temperature range is between 10° C. and 30° C. In another embodiment, the temperature range is between 15° C. and 30° C. In another embodiment, the temperature range is between 20° C. and 30° C. The temperature range employed will depend upon various factors, including but not limited to, the desired storage temperature, the general stability of the protein(s) present in the formulation, the desired mode of administration, and the like.

In yet another preferred embodiment of the methods of the present invention, short term protein stability is determined at 5° C. intervals. In other embodiments, the short term protein stability is determined at 1° C. intervals, or 2° C., 3° C., 4° C., 5° C., 6° C., 7° C., 8° C., 9° C., 10° C., 11° C., 12° C., 13° C., 14° C., 15° C., or greater intervals.

In one embodiment, protein stability is measured by determining the level of enzymatic activity (e.g., the loss in activity) over a given time period. In another embodiment, protein stability is measured by determining the level of protein oligomerization over a given time period. In another embodiment, protein stability is measured by determining the level of protein degradation over a given time period. In yet another embodiment, protein stability is measured by determining two or three of the above stability metrics.

In one embodiment, the protein is an antibody or functional fragment thereof In one embodiment, the antibody is selected from the group consisting of plasma-derived immunoglobulin preparations, recombinant polyclonal or monoclonal preparations, minibodies, diabodies, triabodies, antibody fragments such as Fv, Fab and F(ab)2 or fragmented antibodies such as monovalent or multivalent single chain Fvs (scFv, sc(Fv)2, minibodies, diabodies, and triabodies. In a specific embodiment, the antibody is a recombinant antibody. In another specific embodiment, the antibody is a chimeric antibody. In yet another specific embodiment, the antibody is a humanized antibody. In a preferred embodiment, the antibody is a therapeutic antibody. In another preferred embodiment, the antibody is a diagnostic antibody.

In another embodiment, the protein is a plasma-derived protein. In one embodiment, the plasma-derived protein is selected from the group consisting of Factor II (prothrombin), Factor III (platelet tissue factor), Factor V, Factor VII, Factor VIII, Factor IX, Factor X, Factor XI, Factor XII, Factor XIII, von Willebrand Factor (vWF), Antithrombin III (AT III), Furin, an ADAMTS proteins (i.e., ADAMTS13), a complement factor (i.e., Factor H and Complement factors C1, C2, C2a, C2b, C3, C3a, C3b, C4, C4a, C4b, C5, C5a, and C5b), Alpha-1 antitrypsin (A1A), Albumin, and an Inter-alpha-trypsin Inhibitor (IαI). In one embodiment, the plasma-derived protein is a coagulation factor. In a specific embodiment, the coagulation factor is Factor VIII. In another specific embodiment, the coagulation factor is AT III.

In another embodiment, the protein is a recombinant protein. In one embodiment, the protein is a recombinant blood protein. In one embodiment, the recombinant blood protein is selected from the group consisting of Factor II (prothrombin), Factor III (platelet tissue factor), Factor V, Factor VII, Factor VIII, Factor IX, Factor X, Factor XI, Factor XII, Factor XIII, von Willebrand Factor (vWF), Antithrombin III (AT III), Furin, an ADAMTS proteins (i.e., ADAMTS13), a complement factor (i.e., Factor H and Complement factors C1, C2, C2a, C2b, C3, C3a, C3b, C4, C4a, C4b, C5, C5a, and C5b), Alpha-1 antitrypsin (A1A), Albumin, and an Inter-alpha-trypsin Inhibitor (IαI). In one embodiment, the recombinant blood protein is a coagulation factor. In a specific embodiment, the coagulation factor is Factor VIII. In another specific embodiment, the coagulation factor is AT III.

In one embodiment, wherein the protein is recombinant, the protein is further modified. In a specific embodiment, the protein is modified by conjugation to a water soluble polymer. In one embodiment, the water soluble polymer is selected from a polyalkylene glycol (PAG), a polyethylene glycol (PEG), a hydroxyalkyl starch (HAS), a hydroxyethyl starch (HES), polysialic acid (PSA), and a sugar (e.g., glycosylation).

In yet another aspect, the present invention relates to a method for modeling real-time protein stability, comprising the steps:
(a) determining short term protein stability over the course of 1 to 12 weeks within a temperature range of 4° C. to 60° C. at 5° C. intervals;
(b) plotting the data obtained in step (a) in an Arrhenius plot;
(c) identifying the linear part of the Arrhenius plot obtained in step (b);
(d) determining the highest temperature underlying the linear part of the Arrhenius plot determined in step (c);
(e) performing accelerated stability studies at the temperature determined in step (d); and
(f) determining real-time protein stability based on the accelerated stability data obtained in step (e).

Methods for Determining the Self-Life of a Protein Formulation

In another aspect, the present invention relates to a method for determining the shelf-life of a protein formulation, comprising the steps:
(a) determining short term protein stability within a specific temperature range;
(b) plotting the data obtained in step (a) in an Arrhenius plot;
(c) identifying the linear part of the Arrhenius plot obtained in step (b);
(d) determining the highest temperature underlying the linear part of the Arrhenius plot determined in step (c)

(e) performing an accelerated stability study of the formulation at a temperature equal to or less than the temperature determined in step (d); and
(f) determining the expected shelf-life of the formulation based on the accelerated stability study performed in step (e).

In particular, the highest temperature underlying the linear part of the Arrhenius plot determined in step (b) of the above methods is the highest temperature that is suitable for performing accelerated protein stability studies.

In a preferred embodiment, establishing the Arrhenius plot in step (a) comprises the sub-steps of: (a1) determining short term protein stability within a specific temperature range; and (a2) plotting the data obtained in step (a1) in an Arrhenius plot.

In another preferred embodiment, determining short term protein stability comprises determining protein stability over the course of 1 to 12 weeks. In another embodiment, determining short term protein stability comprises determining protein stability over the course of 2 to 8 weeks. In yet another embodiment, determining short term protein stability comprises determining protein stability over the course of 6 weeks. In yet other, non-limiting embodiments, determining short term protein stability comprises determining protein stability over the course of weeks, i.e., 1, 2, 3, 4, 5, 6, 7, 8, 9, 10, 11, or 12 weeks; or months, i.e., 1, 2, 3, 4, 5, 6, 7, 8, 9, 10, 11, 12, 13, 14, 15, 16, 17, 18, 19, 20, 21, 22, 23, 24, 27, 30, 33, 36, or more months.

In yet another preferred embodiment, short term protein stability is determined in the temperature range of 4° C. to 60° C. In another embodiment, the temperature range is between 20° C. and 60° C. In another embodiment, the temperature range is between 20° C. and 40° C. In another embodiment, the temerature range is between 4° C. and 40° C. In yet another embodiment, the temperature range is between 10° C. and 40° C. In another embodiment, the temperature range is between 15° C. and 40° C. In another embodiment, the temperature range is between 20° C. and 40° C. In another embodiment, the temerature range is between 4° C. and 35° C. In yet another embodiment, the temperature range is between 10° C. and 35° C. In another embodiment, the temperature range is between 15° C. and 35° C. In another embodiment, the temperature range is between 20° C. and 35° C. In another embodiment, the temerature range is between 4° C. and 30° C. In yet another embodiment, the temperature range is between 10° C. and 30° C. In another embodiment, the temperature range is between 15° C. and 30° C. In another embodiment, the temperature range is between 20° C. and 30° C. The temperature range employed will depend upon various factors, including but not limited to, the desired storage temperature, the general stability of the protein(s) present in the formulation, the desired mode of administration, and the like.

In yet another preferred embodiment of the methods of the present invention, short term protein stability is determined at 5° C. intervals. In other embodiments, the short term protein stability is determined at 1° C. intervals, or 2° C., 3° C., 4° C., 5° C., 6° C., 7° C., 8° C., 9° C., 10° C., 11° C., 12° C., 13° C., 14° C., 15° C., or greater intervals.

In one embodiment, protein stability is measured by determining the level of enzymatic activity (e.g., the loss in activity) over a given time period. In another embodiment, protein stability is measured by determining the level of protein oligomerization over a given time period. In another embodiment, protein stability is measured by determining the level of protein degradation over a given time period. In yet another embodiment, protein stability is measured by determining two or three of the above stability metrics.

In one embodiment, the protein is an antibody or functional fragment thereof. In one embodiment, the antibody is selected from the group consisting of plasma-derived immunoglobulin preparations, recombinant polyclonal or monoclonal preparations, minibodies, diabodies, triabodies, antibody fragments such as Fv, Fab and F(ab)2 or fragmented antibodies such as monovalent or multivalent single chain Fvs (scFv, sc(Fv)2, minibodies, diabodies, and triabodies. In a specific embodiment, the antibody is a recombinant antibody. In another specific embodiment, the antibody is a chimeric antibody. In yet another specific embodiment, the antibody is a humanized antibody. In a preferred embodiment, the antibody is a therapeutic antibody. In another preferred embodiment, the antibody is a diagnostic antibody.

In another embodiment, the protein is a plasma-derived protein. In one embodiment, the plasma-derived protein is selected from the group consisting of Factor II (prothrombin), Factor III (platelet tissue factor), Factor V, Factor VII, Factor VIII, Factor IX, Factor X, Factor XI, Factor XII, Factor XIII, von Willebrand Factor (vWF), Antithrombin III (AT III), Furin, an ADAMTS proteins (i.e., ADAMTS13), a complement factor (i.e., Factor H and Complement factors C1, C2, C2a, C2b, C3, C3a, C3b, C4, C4a, C4b, C5, C5a, and C5b), Alpha-1 antitrypsin (A1A), Albumin, and an Inter-alpha-trypsin Inhibitor (I$\alpha$I). In one embodiment, the plasma-derived protein is a coagulation factor. In a specific embodiment, the coagulation factor is Factor VIII. In another specific embodiment, the coagulation factor is AT III.

In another embodiment, the protein is a recombinant protein. In one embodiment, the protein is a recombinant blood protein. In one embodiment, the recombinant blood protein is selected from the group consisting of Factor II (prothrombin), Factor III (platelet tissue factor), Factor V, Factor VII, Factor VIII, Factor IX, Factor X, Factor XI, Factor XII, Factor XIII, von Willebrand Factor (vWF), Antithrombin III (AT III), Furin, an ADAMTS proteins (i.e., ADAMTS13), a complement factor (i.e., Factor H and Complement factors C1, C2, C2a, C2b, C3, C3a, C3b, C4, C4a, C4b, C5, C5a, and C5b), Alpha-1 antitrypsin (A1A), Albumin, and an Inter-alpha-trypsin Inhibitor (I$\alpha$I). In one embodiment, the recombinant blood protein is a coagulation factor. In a specific embodiment, the coagulation factor is Factor VIII. In another specific embodiment, the coagulation factor is AT III.

In one embodiment, wherein the protein is recombinant, the protein is further modified. In a specific embodiment, the protein is modified by conjugation to a water soluble polymer. In one embodiment, the water soluble polymer is selected from a polyalkylene glycol (PAG), a polyethylene glycol (PEG), a hydroxyalkyl starch (HAS), a hydroxyethyl starch (HES), polysialic acid (PSA), and a sugar (e.g., glycosylation).

Methods for Determining the Self-Life of a Factor VIII Formulation

In another aspect, the present invention relates to a method for determining the shelf-life of a Factor VIII formulation, comprising the steps:
(a) determining short term protein stability of the Factor VIII formulation within a specific temperature range;
(b) plotting the data obtained in step (a) in an Arrhenius plot;
(c) identifying the linear part of the Arrhenius plot obtained in step (b);
(d) determining the highest temperature underlying the linear part of the Arrhenius plot determined in step (c)
(e) performing an accelerated stability study of the formulation at a temperature equal to or less than the temperature determined in step (d); and (f) determining the expected shelf-life of the formulation based on the accelerated stability study performed in step (e).

In particular, the highest temperature underlying the linear part of the Arrhenius plot determined in step (b) of the above methods is the highest temperature that is suitable for performing accelerated protein stability studies.

In a preferred embodiment, establishing the Arrhenius plot in step (a) comprises the sub-steps of: (a1) determining short term protein stability within a specific temperature range; and (a2) plotting the data obtained in step (a1) in an Arrhenius plot.

In another preferred embodiment, determining short term protein stability comprises determining protein stability over the course of 1 to 12 weeks. In another embodiment, determining short term protein stability comprises determining protein stability over the course of 2 to 8 weeks. In yet another embodiment, determining short term protein stability comprises determining protein stability over the course of 6 weeks. In yet other, non-limiting embodiments, determining short term protein stability comprises determining protein stability over the course of weeks, i.e., 1, 2, 3, 4, 5, 6, 7, 8, 9, 10, 11, or 12 weeks; or months, i.e., 1, 2, 3, 4, 5, 6, 7, 8, 9, 10, 11, 12, 13, 14, 15, 16, 17, 18, 19, 20, 21, 22, 23, 24, 27, 30, 33, 36, or more months.

In yet another preferred embodiment, short term protein stability is determined in the temperature range of 4° C. to 60° C. In another embodiment, the temperature range is between 20° C. and 60° C. In another embodiment, the temperature range is between 20° C. and 40° C. In another embodiment, the temerature range is between 4° C. and 40° C. In yet another embodiment, the temperature range is between 10° C. and 40° C. In another embodiment, the temperature range is between 15° C. and 40° C. In another embodiment, the temperature range is between 20° C. and 40° C. In another embodiment, the temerature range is between 4° C. and 35° C. In yet another embodiment, the temperature range is between 10° C. and 35° C. In another embodiment, the temperature range is between 15° C. and 35° C. In another embodiment, the temperature range is between 20° C. and 35° C. In another embodiment, the temerature range is between 4° C. and 30° C. In yet another embodiment, the temperature range is between 10° C. and 30° C. In another embodiment, the temperature range is between 15° C. and 30° C. In another embodiment, the temperature range is between 20° C. and 30° C. The temperature range employed will depend upon various factors, including but not limited to, the desired storage temperature, the general stability of the protein(s) present in the formulation, the desired mode of administration, and the like.

In yet another preferred embodiment of the methods of the present invention, short term protein stability is determined at 5° C. intervals. In other embodiments, the short term protein stability is determined at 1° C. intervals, or 2° C., 3° C., 4° C., 5° C., 6° C., 7° C., 8° C., 9° C., 10° C., 11° C., 12° C., 13° C., 14° C., 15° C., or greater intervals.

In one embodiment, the predetermined temperature is between about 2° C. and about 42° C. In one embodiment, the predetermined temperature between about 2° C. and about 8° C. (e.g., refrigerated). In another embodiment, the predetermined temperature between about 20° C. and about 25° C. (e.g., room temperature). In another embodiment, the predetermined temperature between about 28° C. and about 32° C.

In one embodiment, protein stability is measured by determining the level of enzymatic activity (e.g., the loss in activity) over a given time period. In another embodiment, protein stability is measured by determining the level of protein oligomerization over a given time period. In another embodiment, protein stability is measured by determining the level of protein degradation over a given time period. In yet another embodiment, protein stability is measured by determining two or three of the above stability metrics.

In one embodiment, the Factor VIII present in the formulation is further modified. In a specific embodiment, Factor VIII is modified by conjugation to a water soluble polymer. In one embodiment, the water soluble polymer is selected from a polyalkylene glycol (PAG), a polyethylene glycol (PEG), a hydroxyalkyl starch (HAS), a hydroxyethyl starch (HES), polysialic acid (PSA), and a sugar (e.g., glycosylation).

In a related embodiment, the present invention provides a method for determining the shelf-life of a Factor VIII formulation, comprising the steps:
(a) performing an accelerated stability study of the Factor VIII formulation at a temperature equal to or less 30° C.; and
(b) determining the expected shelf-life of the formulation based on the accelerated stability study.

In another embodiment, the accelerated stability study of the Factor VIII formulation is performed at a temperature equal to or less 25° C. In yet another embodiment, the accelerated stability study of the Factor VIII formulation is performed at a temperature equal to or less 20° C. In yet other embodiments, the accelerated stability study of the Factor VIII formulation is performed at a temperature equal to or less about 30° C., or 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., or 10° C.

In one embodiment, the predetermined temperature is between about 2° C. and about 42° C. In one embodiment, the predetermined temperature between about 2° C. and about 8° C. (e.g., refrigerated). In another embodiment, the predetermined temperature between about 20° C. and about 25° C. (e.g., room temperature). In another embodiment, the predetermined temperature between about 28° C. and about 32° C.

In one embodiment, protein stability is measured by determining the level of enzymatic activity (e.g., the loss in activity) over a given time period. In another embodiment, protein stability is measured by determining the level of protein oligomerization over a given time period. In another embodiment, protein stability is measured by determining the level of protein degradation over a given time period. In yet another embodiment, protein stability is measured by determining two or three of the above stability metrics.

In one embodiment, the Factor VIII present in the formulation is further modified. In a specific embodiment, Factor VIII is modified by conjugation to a water soluble polymer. In one embodiment, the water soluble polymer is selected from a polyalkylene glycol (PAG), a polyethylene glycol (PEG), a hydroxyalkyl starch (HAS), a hydroxyethyl starch (HES), polysialic acid (PSA), and a sugar (e.g., glycosylation).

Methods for Determining the Self-Life of an AT III Formulation

In another aspect, the present invention relates to a method for determining the shelf-life of an AT III formulation, comprising the steps:
(a) determining short term protein stability of the AT III formulation within a specific temperature range;
(b) plotting the data obtained in step (a) in an Arrhenius plot;
(c) identifying the linear part of the Arrhenius plot obtained in step (b);
(d) determining the highest temperature underlying the linear part of the Arrhenius plot determined in step (c)

(e) performing an accelerated stability study of the formulation at a temperature equal to or less than the temperature determined in step (d); and (f) determining the expected shelf-life of the formulation based on the accelerated stability study performed in step (e).

In particular, the highest temperature underlying the linear part of the Arrhenius plot determined in step (b) of the above methods is the highest temperature that is suitable for performing accelerated protein stability studies.

In a preferred embodiment, establishing the Arrhenius plot in step (a) comprises the sub-steps of: (a1) determining short term protein stability within a specific temperature range; and (a2) plotting the data obtained in step (a1) in an Arrhenius plot.

In another preferred embodiment, determining short term protein stability comprises determining protein stability over the course of 1 to 12 weeks. In another embodiment, determining short term protein stability comprises determining protein stability over the course of 2 to 8 weeks. In yet another embodiment, determining short term protein stability comprises determining protein stability over the course of 6 weeks. In yet other, non-limiting embodiments, determining short term protein stability comprises determining protein stability over the course of weeks, i.e., 1, 2, 3, 4, 5, 6, 7, 8, 9, 10, 11, or 12 weeks; or months, i.e., 1, 2, 3, 4, 5, 6, 7, 8, 9, 10, 11, 12, 13, 14, 15, 16, 17, 18, 19, 20, 21, 22, 23, 24, 27, 30, 33, 36, or more months.

In yet another preferred embodiment, short term protein stability is determined in the temperature range of 4° C. to 60° C. In another embodiment, the temperature range is between 20° C. and 60° C. In another embodiment, the temperature range is between 20° C. and 40° C. In another embodiment, the temerature range is between 4° C. and 40° C. In yet another embodiment, the temperature range is between 10° C. and 40° C. In another embodiment, the temperature range is between 15° C. and 40° C. In another embodiment, the temperature range is between 20° C. and 40° C. In another embodiment, the temerature range is between 4° C. and 35° C. In yet another embodiment, the temperature range is between 10° C. and 35° C. In another embodiment, the temperature range is between 15° C. and 35° C. In another embodiment, the temperature range is between 20° C. and 35° C. In another embodiment, the temerature range is between 4° C. and 30° C. In yet another embodiment, the temperature range is between 10° C. and 30° C. In another embodiment, the temperature range is between 15° C. and 30° C. In another embodiment, the temperature range is between 20° C. and 30° C. The temperature range employed will depend upon various factors, including but not limited to, the desired storage temperature, the general stability of the protein(s) present in the formulation, the desired mode of administration, and the like.

In yet another preferred embodiment of the methods of the present invention, short term protein stability is determined at 5° C. intervals. In other embodiments, the short term protein stability is determined at 1° C. intervals, or 2° C., 3° C., 4° C., 5° C., 6° C., 7° C., 8° C., 9° C., 10° C., 11° C., 12° C., 13° C., 14° C., 15° C., or greater intervals.

In one embodiment, the predetermined temperature is between about 2° C. and about 42° C. In one embodiment, the predetermined temperature between about 2° C. and about 8° C. (e.g., refrigerated). In another embodiment, the predetermined temperature between about 20° C. and about 25° C. (e.g., room temperature). In another embodiment, the predetermined temperature between about 28° C. and about 32° C.

In one embodiment, protein stability is measured by determining the level of enzymatic activity (e.g., the loss in activity) over a given time period. In another embodiment, protein stability is measured by determining the level of protein oligomerization over a given time period. In another embodiment, protein stability is measured by determining the level of protein degradation over a given time period. In yet another embodiment, protein stability is measured by determining two or three of the above stability metrics.

In one embodiment, the AT III present in the formulation is further modified. In a specific embodiment, AT III is modified by conjugation to a water soluble polymer. In one embodiment, the water soluble polymer is selected from a polyalkylene glycol (PAG), a polyethylene glycol (PEG), a hydroxyalkyl starch (HAS), a hydroxyethyl starch (HES), polysialic acid (PSA), and a sugar (e.g., glycosylation).

In a related embodiment, the present invention provides a method for determining the shelf-life of an AT III formulation, comprising the steps:

(a) performing an accelerated stability study of the AT III formulation at a temperature equal to or less 20° C.; and (b) determining the expected shelf-life of the formulation based on the accelerated stability study.

In another embodiment, the accelerated stability study of the Factor AT III formulation is performed at a temperature equal to or less 15° C. In yet another embodiment, the accelerated stability study of the Factor VIII formulation is performed at a temperature equal to or less 10° C. In yet other embodiments, the accelerated stability study of the Factor VIII formulation is performed at a temperature equal to or less about 25° C., or 24° C., 23° C., 22° C., 21° C., 20° C., 19° C., 18° C., 17° C., 16° C., 15° C., 14° C., 13° C., 12° C., 11° C., or 10° C.

In one embodiment, the predetermined temperature is between about 2° C. and about 42° C. In one embodiment, the predetermined temperature is between about 2° C. and about 8° C. (e.g., refrigerated). In another embodiment, the predetermined temperature is between about 20° C. and about 25° C. (e.g., room temperature). In another embodiment, the predetermined temperature is between about 28° C. and about 32° C.

In one embodiment, protein stability is measured by determining the level of enzymatic activity (e.g., the loss in activity) over a given time period. In another embodiment, protein stability is measured by determining the level of protein oligomerization over a given time period. In another embodiment, protein stability is measured by determining the level of protein degradation over a given time period. In yet another embodiment, protein stability is measured by determining two or three of the above stability metrics.

In one embodiment, the AT III present in the formulation is further modified. In a specific embodiment, AT III is modified by conjugation to a water soluble polymer. In one embodiment, the water soluble polymer is selected from a polyalkylene glycol (PAG), a polyethylene glycol (PEG), a hydroxyalkyl starch (HAS), a hydroxyethyl starch (HES), polysialic acid (PSA), and a sugar (e.g., glycosylation).

Measurement of Protein Stability

Protein stability may be measured using various metrics, including but not limited to, the extent or rate of protein aggregation, the loss of enzymatic activity, the loss of protein binding, the loss of substrate binding, the loss of anti-antigen titer, and/or the extent or rate of protein degradation. One of skill in the art will recognize that certain metrics will be more or less relevant to individual proteins. For example, the stability of an enzyme may be determined by monitoring the loss of enzymatic activity over time, but not by monitoring the loss of an anti-antigen titer. Conversely, the stability of an antibody may be measured by monitoring the loss of anti-antigen titer, but not by enzymatic activity.

In one embodiment, the stability of a protein formulation may be determined by monitoring the extent or rate of protein aggregation within the formulation. Protein aggregation may be determined for example, by size exclusion chromatography (SEC), high performance size exclusion chromatography (HP-SEC), dynamic light scattering, non-denaturing gel electrophoresis and the like. Although the absolute aggregation level at which a protein composition will be considered unstable will vary from protein to protein, the level of aggregation that results in a significant loss of the therapeutic value of the composition will generally be regarded as unstable.

In another embodiment, wherein the protein is an enzyme, the stability of the formulation may be determined by monitoring the loss of bulk enzymatic activity in the preparation. For example, in one embodiment, a 20% loss of enzymatic activity will correspond to an unstable composition. In other embodiments, a 10% loss of enzymatic activity, or a 15%, 20%, 25%, 30%, 35%, 40%, 45%, 50%, or higher loss of enzymatic activity will correspond to an unstable composition.

In one embodiment, wherein the protein is an antibody or fragment thereof, the stability of the composition may be determined by monitoring the loss of anti-antigen titer. The level of anti-antigen titer may be determined, for example, by an immunoassay. A variety of immunoassay formats may be used for this purpose. For example, solid-phase ELISA immunoassays are routinely used to determine antigen titer (see, e.g., Harlow & Lane, *Using Antibodies, A Laboratory Manual* (1998) for a description of immunoassay formats and conditions that can be used to determine specific immunoreactivity). In one embodiment, a 20% loss of anti-antigen titer will correspond to an unstable composition. In other embodiments, a 10% loss of anti-antigen titer, or a 15%, 20%, 25%, 30%, 35%, 40%, 45%, 50%, or higher loss of anti-antigen titer will correspond to an unstable composition.

In another embodiment, the stability of a protein formulation may be determined by monitoring the extent or rate of protein degradation within the formulation. Protein degradation may be determined for example, by size exclusion chromatography (SEC), high performance size exclusion chromatography (HP-SEC), dynamic light scattering, non-denaturing gel electrophoresis and the like. Although the absolute degradation level at which a protein composition will be considered unstable will vary from protein to protein, the level of degradation that results in a significant loss of the therapeutic value of the composition will generally be regarded as unstable.

Protein Formulations

The stability profile of any protein formulation may be determined using the methods provided herein. Methods and general principals for formulating protein compositions are well known in the art (for review, see, McNally and Hastedt, *Protein Formulation and Delivery*, second edition (2007), the disclosure of which is hereby incorporated by reference in its entirety for all purposes). Generally, the protein formulation may contain one or more of the following components: buffers (i.e., tris, glycine, histidine, or other amino acids, salts like citrate, phosphate, acetate, glutamate, tartrate, benzoate, lactate, gluconate, malate, succinate, formate, propionate, carbonate, and the like); salts; antioxidants (i.e., sodium bisulfate, ascorbic acid, ascorbyl palmitate, citric acid, butylated hydroxyanisole, butylated hydroxytoluene, hydrophosphorous acid, monothioglycerol, propyl gallate, methionine, sodium ascorbate, sodium citrate, sodium sulfide, sodium sulfite, sodium bisulfite, sodium formaldehyde sulfoxylate, thioglycolic acid, sodium metabisulfite, EDTA (edetate), penetrate, and the like); bulking agents (i.e., dextran, trehalose, sucrose, polyvinylpyrrolidone, lactose, inositol, sorbitol, dimethylsulfoxide, glycerol, albumin, calcium lactobionate, and the like); cryoprotectants (i.e., polysorbate, poloxamer, polyethylene glycol, trehalose, and the like); sugars; polyols; amino acids; and surfactants (i.e., polysorbates, polyoxyethylene alkyl ethers such as Brij 35®, or poloxamer such as Tween 20, Tween 80, or poloxamer 188. Preferred detergents are poloxamers, e.g., Poloxamer 188, Poloxamer 407; polyoxyethylene alkyl ethers, e.g., Brij 35®, Cremophor A25, Sympatens ALM/230; and polysorbates/Tweens, e.g., Polysorbate 20, Polysorbate 80, and Poloxamers, e.g., Poloxamer 188, and Tweens, e.g., Tween 20 and Tween 80).

EXAMPLES

Example 1

Real-Time Stability of a Liquid Antithrombin III Formulation

Stability of a liquid Antithrombin III (AT III) formulation at elevated temperatures was determined to be about 10 days at 40° C. and about 45 days at 25° C. Prediction of real-time stability at 4° C., based on this accelerated protein stability data under the assumption of a linear Arrhenius plot at these elevated temperatures, results in a predicted stability at 4° C. of about 4 to 6 months. However, long-term studies showed a stability of the above AT III formulation at 4° C. of about 14 months. The conclusion drawn from these data is that protein stability determinations derived from protein stability data at elevated temperatures cannot necessarily be extrapolated to lower temperatures, since the assumption of linearity of the Arrhenius plot at elevated temperatures may not be correct.

Example 2

Short Term Stability Determination of a Liquid Antithrombin III Formulation

Short term stability of the above liquid AT III formulation was determined over the course of 6 weeks at temperatures of 4° C., 15° C., 20° C., 25° C., 30° C., 37° C. and 40° C. Activity data at the different temperatures over time is shown in Tables 1 to 7.

TABLE 1

AT III activity at 4° C. over time

| t [weeks] | absolute activity | remaining activity [%] |
|---|---|---|
| 0 | 52.77 | 100.0 |
| 1 | 53.07 | 100.6 |
| 2 | 49.89 | 94.5 |
| 3 | 51.76 | 98.1 |
| 4 | 51.43 | 97.5 |
| 5 | 50.92 | 96.5 |
| 6 | 46.61 | 88.3 |

TABLE 2

AT III activity at 15° C. over time

| t [weeks] | absolute activity | remaining activity [%] |
|---|---|---|
| 0 | 52.77 | 100.0 |
| 1 | 49.83 | 94.4 |
| 2 | 60.8 | 115.1 |

TABLE 2-continued

AT III activity at 15° C. over time

| t [weeks] | absolute activity | remaining activity [%] |
|---|---|---|
| 3 | 47.9 | 90.7 |
| 4 | 51.6 | 97.8 |
| 5 | 48.3 | 91.5 |
| 6 | 45.0 | 85.3 |

TABLE 3

AT III activity at 20° C. over time

| t [weeks] | absolute activity | remaining activity [%] |
|---|---|---|
| 0 | 52.77 | 100.0 |
| 1 | 51.71 | 98.0 |
| 2 | 52.8 | 100.1 |
| 3 | 47.7 | 90.4 |
| 4 | 50.8 | 96.2 |
| 5 | 47.5 | 90.1 |
| 6 | 43.9 | 83.1 |

TABLE 4

AT III activity at 25° C. over time

| t [weeks] | absolute activity | remaining activity [%] |
|---|---|---|
| 0 | 52.77 | 100.0 |
| 1 | 48.28 | 91.5 |
| 2 | 50.6 | 95.9 |
| 3 | 47.3 | 89.6 |
| 4 | 46.8 | 88.8 |
| 5 | 44.2 | 83.8 |
| 6 | 38.8 | 73.6 |

TABLE 5

AT III activity at 30° C. over time

| t [weeks] | absolute activity | remaining activity [%] |
|---|---|---|
| 0 | 52.77 | 100.0 |
| 1 | 51.919 | 98.4 |
| 2 | 50.866 | 96.4 |
| 3 | 42.186 | 79.9 |
| 4 | 41.188 | 78.1 |
| 5 | 37.689 | 71.4 |
| 6 | 38.791 | 73.5 |

TABLE 6

AT III activity at 37° C. over time

| t [weeks] | absolute activity | remaining activity [%] |
|---|---|---|
| 0 | 52.77 | 100.0 |
| 1 | 46.20 | 87.5 |
| 2 | 43.989 | 83.4 |
| 3 | 34.685 | 65.7 |
| 4 | 31.245 | 59.2 |
| 5 | 29.147 | 55.2 |
| 6 | 23.356 | 44.3 |

TABLE 7

AT III activity at 40° C. over time

| t [weeks] | absolute activity | remaining activity [%] |
|---|---|---|
| 0 | 52.77 | 100.0 |
| 1 | 36.864 | 69.9 |
| 2 | 32.309 | 61.2 |
| 3 | 23.507 | 44.5 |
| 4 | 21.052 | 39.9 |
| 5 | 20.894 | 39.6 |
| 6 | 9.344 | 17.7 |

Determination of the respective rate constants of protein activity loss k is shown if FIG. 1. The rate constants k and their natural logarithm ln k, as well as normal and reciprocal temperatures (T and 1/T, respectively) are shown in Table 8.

TABLE 8

Rate constants of protein activity loss at the respective temperatures

| T [° C.] | k | 1/T | ln k |
|---|---|---|---|
| 4 | 1.4382 | 0.250 | 0.3634 |
| 15 | 2.4065 | 0.067 | 0.8782 |
| 20 | 2.5128 | 0.050 | 0.9214 |
| 25 | 3.6365 | 0.040 | 1.2910 |
| 30 | 5.4194 | 0.033 | 1.6900 |
| 37 | 9.1424 | 0.027 | 2.2129 |
| 40 | 11.741 | 0.025 | 2.4631 |

Example 3

Determining the Highest Temperature

Figure 2:
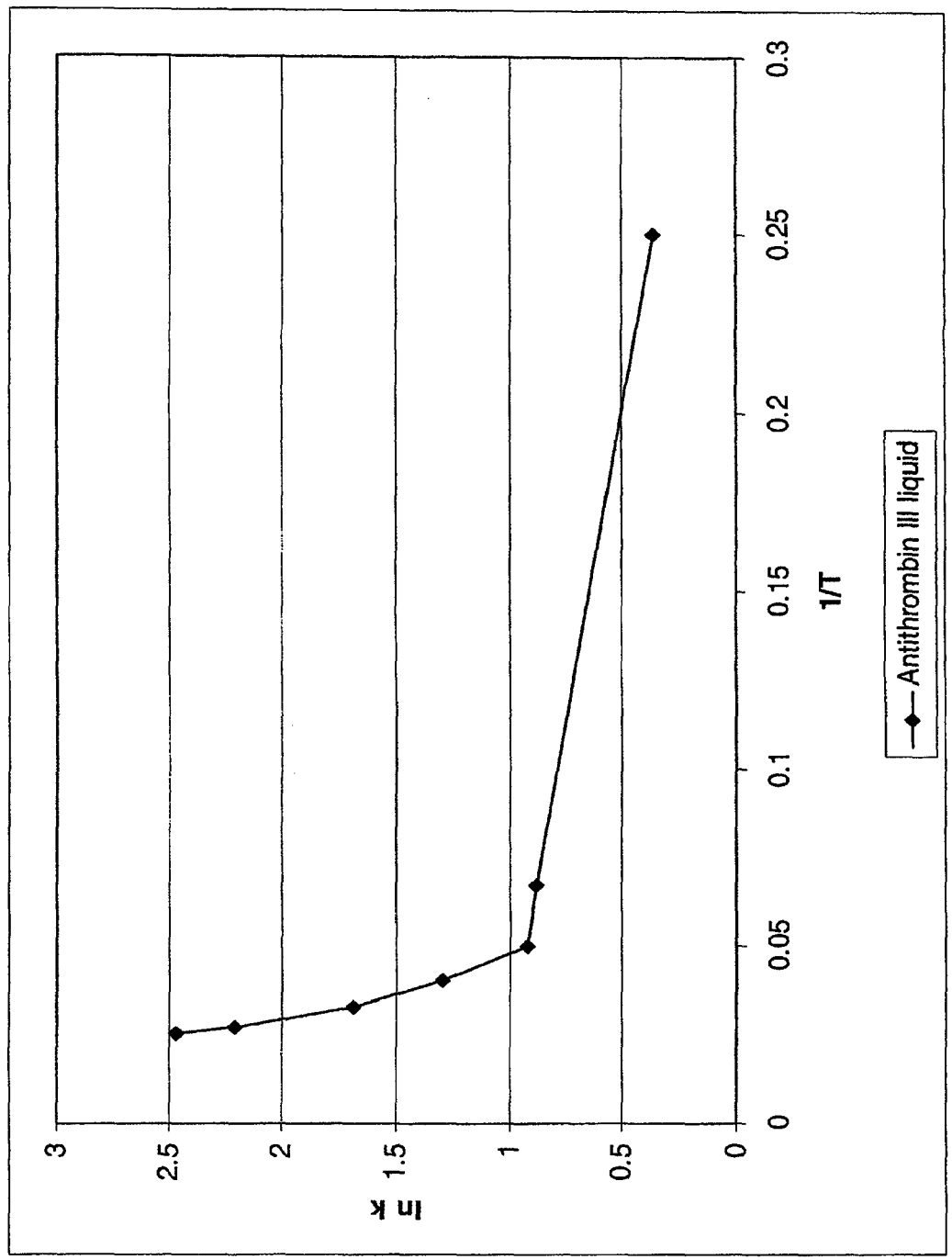
FIG. 2 shows the Arrhenius plot for the liquid AT III formulation based on the data shown in FIG. 1. The linear part of the Arrhenius plot can be determined visually. The lowest 1/T value underlying this linear part is 1/T=0.05, corresponding to a temperature of T=20° C.

FIG. 2 shows the Arrhenius plot for the data summarized in Table 8. As expected for a protein stability Arrhenius plot, the plot shows a linear part at the higher 1/T values (i.e. the lower temperatures T) and a non-linear part at the lower 1/T values (i.e. the higher temperatures T). The linear part of the Arrhenius plot can easily be determined visually to be the part between 1/T=0.050 and 1/T=0.250, corresponding to temperatures T between 4° C. and 20° C. Therefore, only accelerated stability data generated within this temperature range can be used for determining real-time stability. Accordingly, the highest temperature T underlying the linear part of the Arrhenius plot, which is the highest temperature that is suitable for performing accelerated protein stability studies, is T=20° C. Thus, accelerated stability studies for this particular protein should be performed at a maximum temperature of T=20° C. as determined by the method of the present invention. Accelerated stability data obtained at that temperature can correctly be extrapolated to different temperatures, since the underlying Arrhenius plot is linear for T≤20° C.

Example 4

Short Term Stability of Liquid Recombinant Factor VIII (rFVIII) Conjugates

Short term stability of two liquid rFVIII conjugate formulations was determined over the course of 4 weeks at temperatures of 4° C., 30° C., and over the course of 2 weeks at a temperature of 40° C. Activity data of both formulations at the different temperatures over time are shown in Tables 9 to 11.

TABLE 9 rFVIII activity at 4° C. over time

| | Formulation 1 (F1) | | Formulation 2 (F2) | |
| --- | --- | --- | --- | --- |
| t [weeks] | abs. activity | remaining activity [%] | abs. activity | remaining activity [%] |
| 0 | 139.92 | 100 | 99.16 | 100 |
| 1 | 131.46 | 94 | 134.96 | 136 |
| 2 | 110.02 | 79 | 92.00 | 93 |
| 3 | 107.15 | 77 | 120.39 | 121 |
| 4 | 92.07 | 66 | 97.23 | 98 |

TABLE 10 rFVIII activity at 30° C. over time

| | Formulation 1 (F1) | | Formulation 2 (F2) | |
| --- | --- | --- | --- | --- |
| t [weeks] | abs. activity | remaining activity [%] | abs. activity | remaining activity [%] |
| 0 | 139.92 | 100 | 99.16 | 100 |
| 1 | 104.85 | 75 | 100.80 | 102 |
| 2 | 64.87 | 46 | 58.89 | 59 |
| 3 | 55.10 | 39* | 42.09 | 42 |
| 4 | 38.50 | 28 | 30.01 | 30 |

TABLE 11 rFVIII activity at 40° C. over time

| | Formulation 1 (F1) | | Formulation 2 (F2) | |
| --- | --- | --- | --- | --- |
| t [weeks] | abs. activity | remaining activity [%] | abs. activity | remaining activity [%] |
| 0 | 139.92 | 100 | 99.16 | 100 |
| 1 | 37.96 | 27 | 34.66 | 35 |
| 2 | 19.79 | 14 | 16.87 | 17 |

Figure 3:
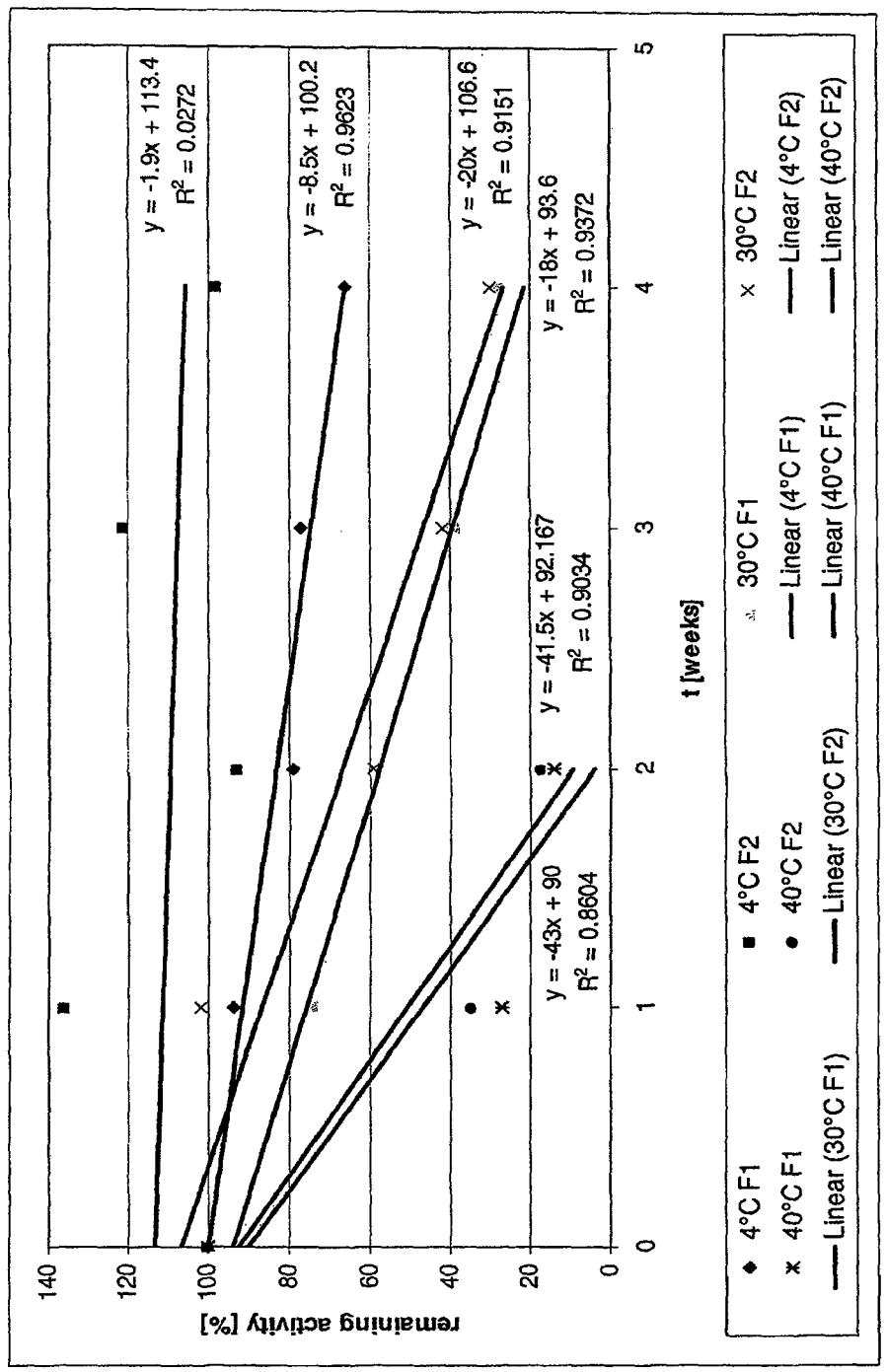
FIG. 3 shows the short term stability of two liquid recombinant Factor VIII (rFVIII) conjugate formulations at different temperatures over time. The equations for the linear regression curves are shown. The rate constant of protein activity loss k corresponds to the negative ascent of these linear regression curves.

Determination of the respective rate constants of protein activity loss k for both formulations is shown in FIG. 3. The rate constants k and their natural logarithm ln k, as well as normal and reciprocal temperatures (T and 1/T, respectively) are shown in Table 12.

TABLE 12

Rate constants of protein activity loss at the respective temperatures

| | | Formulation 1 (F1) | | Formulation 2 (F2) | |
| --- | --- | --- | --- | --- | --- |
| T [° C.] | 1/T | k | ln k | k | ln k |
| 4 | 0.250 | 8.5 | 2.14 | 1.9 | 0.64 |
| 30 | 0.033 | 18.0 | 2.89 | 20.0 | 3.00 |
| 40 | 0.025 | 41.5 | 3.73 | 43.0 | 3.76 |

Example 5

Determining the Highest Temperature

Figure 4:
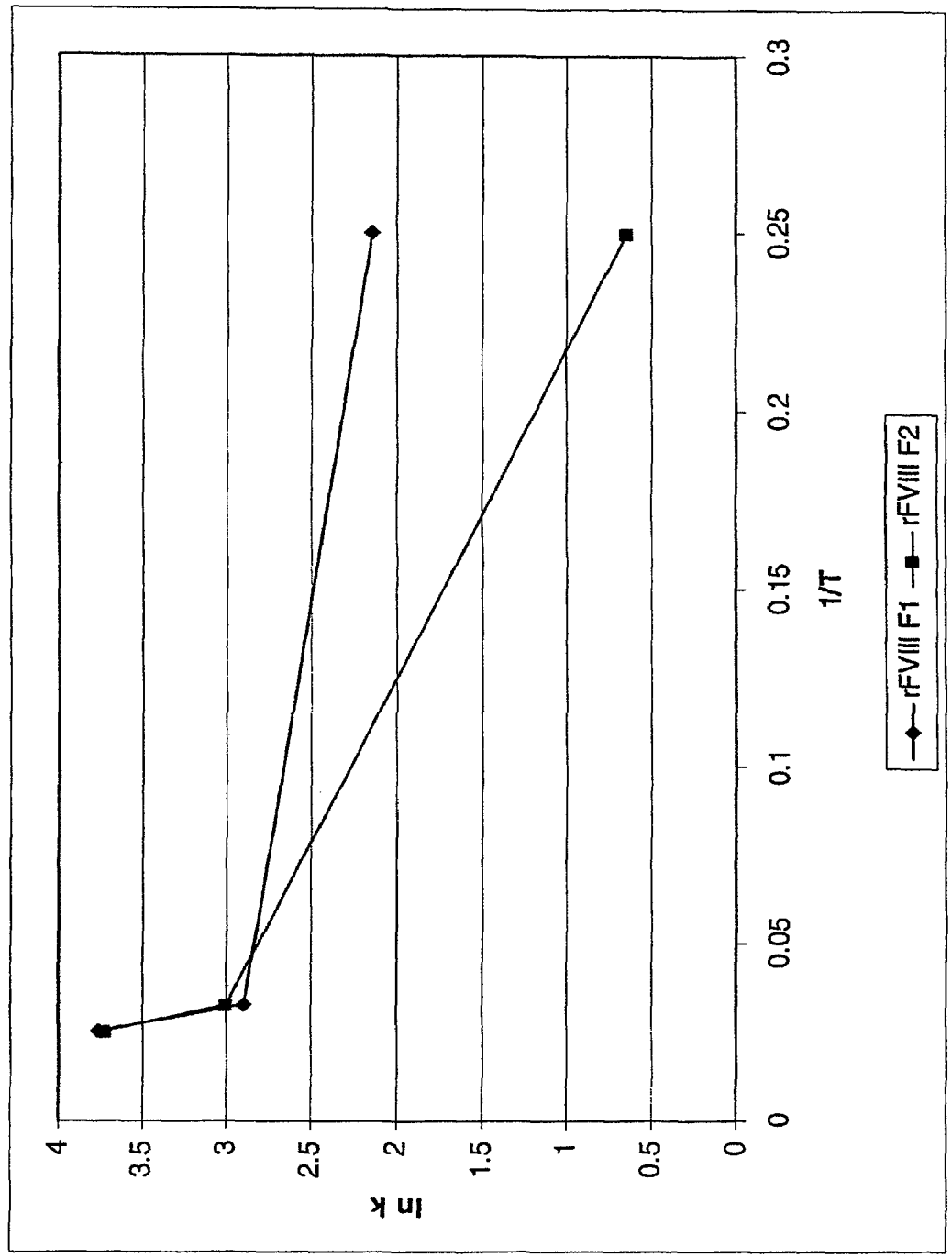
FIG. 4 shows the Arrhenius plots for the liquid rFVIII conjugate formulations based on the data shown in FIG. 3. The highest 1/T value, 1/T=0.025, corresponding to a temperature of T=40° C., is clearly outside of the linear part of the Arrhenius plots.

FIG. 4 shows the Arrhenius plots for the data summarized in Table 12. As expected, the Arrhenius plots are not linear. In particular, the values for 1/T=0.25, corresponding to a temperature T=40° C., are clearly outside of the linear part. Therefore, accelerated stability studies for this particular protein should be performed at lower temperatures.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for modeling protein stability over time, comprising the steps:
    (a) determining a stability of a protein at a plurality of different temperatures within a specific temperature range, wherein the protein stability comprises a measure of retention of enzymatic activity over time;
    (b) creating an Arrhenius plot comprising the stability of the protein at the plurality of temperatures determined in step (a), the Arrhenius plot having a linear portion at lower temperatures and a non-linear portion at higher temperatures, the linear and non-linear portions joining at an inflection point on the Arrhenius plot;
    (c) identifying the inflection point at the junction between the linear portion and the non-linear portion of the Arrhenius plot created in step (b);
    (d) determining an assay temperature consisting of the temperature at the inflection point of the Arrhenius plot created in step (b);
    (e) performing an accelerated stability study of the protein at the assay temperature determined in step (d), wherein the stability study comprises determining a retention of enzymatic activity over time; and
    (f) determining a stability of the protein at a second temperature based on the accelerated stability data obtained in step (e), wherein the second temperature is lower than the assay temperature.

2. The method of claim 1, wherein the protein stability determined in step (a) is determined over a time course of from 1 to 12 weeks.

3. The method of claim 1, wherein each respective temperature in the plurality of temperatures used in step (a) is in the temperature range of from 4° C. to 60° C.

4. The method of claim 1, wherein the method further comprises determining an expected shelf-life of the protein at a predetermined temperature below the assay temperature, wherein the expected shelf-life is the period of time a formulation comprising the protein is expected to maintain a predetermined level of stability.

5. The method of claim 4, wherein the predetermined level of stability is a threshold level of enzymatic activity.

6. The method of claim 4, wherein the predetermined level of stability is a threshold level of protein aggregation.

7. The method of claim 4, wherein the predetermined level of stability is a threshold level of protein degradation.

8. The method of claim 4, wherein the predetermined temperature is between 2° C. and 8° C.

9. The method of claim 4, wherein the protein is an antibody.

10. The method of claim 9, wherein the antibody is a recombinant antibody.

11. The method of claim 4, wherein the protein is a plasma-derived protein.

12. The method of claim 4, wherein the protein is Factor VIII.

13. The method of claim 4, wherein the protein is anti-thrombin III (AT III).

14. A method for modeling protein stability over time, comprising the steps:
  (a) determining a stability of a protein at a plurality of different temperatures within a specific temperature range, wherein the protein stability comprises a measure of retention of enzymatic activity over time;
  (b) creating an Arrhenius plot comprising the stability of the protein at the plurality of temperatures determined in step (a), the Arrhenius plot having a linear portion at lower temperatures and a non-linear portion at higher temperatures, the linear and non-linear portions joining at an inflection point on the Arrhenius plot;
  (c) identifying the inflection point at the junction between the linear portion and the non-linear portion of the Arrhenius plot created in step (b);
  (d) determining an assay temperature consisting of the temperature at the inflection point of the Arrhenius plot created in step (b);
  (e) performing an accelerated stability study of the protein at the assay temperature determined in step (d), wherein the stability study comprises determining a retention of enzymatic activity over time; and
  (f) determining a stability of the protein at a second temperature based on the accelerated stability data obtained in step (e), wherein the second temperature is lower than the assay temperature,
  wherein the respective temperatures in the plurality of temperatures used in step (a) are at 5° C. intervals.

15. A method for determining the shelf-life of Factor VIII formulation, comprising the steps:
  (a) performing an accelerated stability study of the Factor VII formulation at a temperature equal to or less 30° C.; and
  (b) determining the expected shelf-life of the formulation based on the accelerated stability study.

16. The method of claim 15, wherein the accelerated stability study is performed at a temperature equal to or less 25° C.

17. A method for determining the shelf-life of an anti-thrombin III (AT III) formulation, comprising the steps:
  (a) performing an accelerated stability study of the AT III formulation at a temperature equal to or less 20° C.; and
  (b) determining the expected shelf-life of the formulation based on the accelerated stability study.

18. The method of claim 17, wherein the accelerated stability study is performed at a temperature equal to or less 15° C.

19. A method for modeling protein stability over time, comprising the steps:
  (a) determining a stability of a protein at a plurality of different temperatures within a specific temperature range, wherein the protein stability comprises a measure of protein aggregation over time;
  (b) creating an Arrhenius plot comprising the stability of the protein at the plurality of temperatures determined in step (a), the Arrhenius plot having a linear portion at lower temperatures and a non-linear portion at higher temperatures, the linear and non-linear portions joining at an inflection point on the Arrhenius plot;
  (c) identifying the inflection point at the junction between the linear portion and the non-linear portion of the Arrhenius plot created in step (b);
  (d) determining an assay temperature consisting of the temperature at the inflection point of the Arrhenius plot created in step (b);
  (e) performing an accelerated stability study of the protein at the assay temperature determined in step (d), wherein the stability study comprises determining protein aggregation over time; and
  (f) determining a stability of the protein at a second temperature based on the accelerated stability data obtained in step (e), wherein the second temperature is lower than the assay temperature.

20. A method for modeling protein stability over time, comprising the steps:
  (a) determining a stability of a protein at a plurality of different temperatures within a specific temperature range, wherein the protein stability comprises a measure of protein degradation over time;
  (b) creating an Arrhenius plot comprising the stability of the protein at the plurality of temperatures determined in step (a), the Arrhenius plot having a linear portion at lower temperatures and a non-linear portion at higher temperatures, the linear and non-linear portions joining at an inflection point on the Arrhenius plot;
  (c) identifying the inflection point at the junction between the linear portion and the non-linear portion of the Arrhenius plot created in step (b);
  (d) determining an assay temperature consisting of the temperature at the inflection point of the Arrhenius plot created in step (b);
  (e) performing an accelerated stability study of the protein at the assay temperature determined in step (d), wherein the stability study comprises determining protein degradation over time; and
  (f) determining a stability of the protein at a second temperature based on the accelerated stability data obtained in step (e), wherein the second temperature is lower than the assay temperature.

* * * * *